United States Patent
Stancer et al.

(10) Patent No.: US 9,095,721 B2
(45) Date of Patent: Aug. 4, 2015

(54) UNIPOLAR PACING IN THE PRESENCE OF ELECTROMAGNETIC INTERFERENCE

(76) Inventors: Christopher C. Stancer, Prescott, WI (US); Jonathan D. Edmonson, Blaine, MN (US); Michael L. Ellingson, St. Louis Park, MN (US)

( * ) Notice: Subject to any disclaimer, the term of this patent is extended or adjusted under 35 U.S.C. 154(b) by 667 days.

(21) Appl. No.: 13/299,965

(22) Filed: Nov. 18, 2011

(65) Prior Publication Data

US 2012/0277815 A1 Nov. 1, 2012

Related U.S. Application Data

(60) Provisional application No. 61/480,749, filed on Apr. 29, 2011.

(51) Int. Cl.
*A61N 1/08* (2006.01)
*A61N 1/37* (2006.01)

(52) U.S. Cl.
CPC ......... *A61N 1/3718* (2013.01); *A61N 2001/086* (2013.01)

(58) Field of Classification Search
CPC .................... A61B 2018/1293; A61N 1/3688
USPC ................................ 607/6, 7, 62, 28; 600/425
See application file for complete search history.

(56) References Cited

U.S. PATENT DOCUMENTS

| | | |
|---|---|---|
| 4,344,437 A | 8/1982 | Markowitz |
| 4,878,497 A | 11/1989 | Callaghan et al. |
| 5,076,272 A | 12/1991 | Ferek-Petric |
| 5,431,692 A | 7/1995 | Hansen et al. |
| 5,480,414 A * | 1/1996 | Stroebel et al. ................. 607/28 |
| 5,607,458 A | 3/1997 | Causey, III et al. |
| 5,817,136 A | 10/1998 | Nappholz et al. |
| 5,846,264 A | 12/1998 | Andersson et al. |
| 5,928,271 A | 7/1999 | Hess et al. |
| 6,061,594 A | 5/2000 | Zhu et al. |
| 6,188,926 B1 | 2/2001 | Vock |
| 6,678,560 B1 * | 1/2004 | Gilkerson et al. .............. 607/14 |

(Continued)

FOREIGN PATENT DOCUMENTS

WO 2010039877 A1 4/2010

OTHER PUBLICATIONS

St. Jude Medical Presentation, "The Electrical Management of Cardiac Rhythm Disorders Bradycardia Autocapture™ Pacing Systems," Jan. 1, 2008, 38 pages.

(Continued)

*Primary Examiner* — Christopher D Koharski
*Assistant Examiner* — Natasha Patel
(74) *Attorney, Agent, or Firm* — Michael J. Ostrom

(57) ABSTRACT

An implantable medical system may include an implantable medical lead including at least one electrode and an implantable medical device. The implantable medical device comprises an electromagnetic interference (EMI) detection module that monitors for one or more particular characteristics of EMI. A control module is configured to control a therapy module to generate single stimulation pulses while operating the IMD in a first operating mode. In response to detecting the condition indicative of the presence of EMI, the control module switches the IMD from the first operating mode to a second operating mode and generates at least one group of two or more stimulation pulses in close proximity to one another in place of a single stimulation pulse while operating the IMD in the second operating mode.

26 Claims, 9 Drawing Sheets

(56) References Cited

U.S. PATENT DOCUMENTS

| | | |
|---|---|---|
| 6,856,835 B2 | 2/2005 | Bardy et al. |
| 7,031,773 B1 | 4/2006 | Levine et al. |
| 7,146,212 B2 | 12/2006 | Bardy et al. |
| 7,212,855 B1 | 5/2007 | Kroll et al. |
| 7,225,020 B1 | 5/2007 | Kroll et al. |
| 7,363,081 B1 | 4/2008 | Kroll et al. |
| 7,424,323 B1 | 9/2008 | Reiss et al. |
| 7,474,247 B1 | 1/2009 | Heinks et al. |
| 7,561,915 B1 | 7/2009 | Cooke et al. |
| 7,693,568 B2 | 4/2010 | Zeijlemaker |
| 2001/0034538 A1 | 10/2001 | Olson et al. |
| 2003/0083712 A1 | 5/2003 | Rueter et al. |
| 2003/0144698 A1 | 7/2003 | Ujhelyi et al. |
| 2004/0039422 A1 | 2/2004 | Russie et al. |
| 2004/0162593 A1 | 8/2004 | Jorgenson et al. |
| 2004/0254614 A1 | 12/2004 | Spinelli et al. |
| 2005/0038474 A1 | 2/2005 | Wool |
| 2005/0137640 A1 | 6/2005 | Freeberg et al. |
| 2006/0074454 A1 | 4/2006 | Freeberg |
| 2006/0167496 A1 | 7/2006 | Nelson et al. |
| 2006/0173493 A1 | 8/2006 | Armstrong et al. |
| 2006/0247697 A1 | 11/2006 | Sharma et al. |
| 2006/0293717 A1 | 12/2006 | Sathaye et al. |
| 2007/0203523 A1 | 8/2007 | Betzold |
| 2007/0293898 A1 | 12/2007 | Sheldon et al. |
| 2007/0293899 A1 | 12/2007 | Sheldon et al. |
| 2008/0071319 A1 | 3/2008 | Sathaye et al. |
| 2008/0103536 A1 | 5/2008 | Xiao |
| 2008/0103537 A1 | 5/2008 | Sigg et al. |
| 2009/0138058 A1* | 5/2009 | Cooke et al. .................... 607/5 |
| 2009/0149905 A1 | 6/2009 | Lyden et al. |
| 2009/0157135 A1 | 6/2009 | Perschbacher et al. |
| 2010/0010554 A1 | 1/2010 | Reiss |
| 2010/0087892 A1 | 4/2010 | Stubbs et al. |
| 2010/0094370 A1 | 4/2010 | Levin et al. |
| 2010/0106209 A1* | 4/2010 | Gunderson et al. ............. 607/17 |
| 2010/0114199 A1 | 5/2010 | Krause et al. |
| 2010/0114224 A1 | 5/2010 | Krause et al. |
| 2010/0137945 A1 | 6/2010 | Gadagkar et al. |
| 2010/0191236 A1 | 7/2010 | Johnson et al. |
| 2010/0198310 A1 | 8/2010 | Ellingson |
| 2010/0292745 A1 | 11/2010 | Shuros et al. |

OTHER PUBLICATIONS (PCT/US2012/020396) PCT Notification of Transmittal of the International Search Report and the Written Opinion of the International Searching Authority, 12 pages.

\* cited by examiner

UNIPOLAR PACING IN THE PRESENCE OF ELECTROMAGNETIC INTERFERENCE

This application claims the benefit of U.S. Provisional Application No. 61/480,749, filed on Apr. 29, 2011, the content of which is incorporated herein by reference in its entirety.

TECHNICAL FIELD

This disclosure relates generally to implantable medical systems. More particularly, this disclosure describes techniques for pacing in the presence of electromagnetic interference (EMI).

BACKGROUND

A wide variety of implantable medical systems that deliver a therapy or monitor a physiologic condition of a patient have been clinically implanted or proposed for clinical implantation in patients. The implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. Implantable leads are also used in neurological devices, muscular stimulation therapy, gastric system stimulators and other implantable medical devices (IMDs).

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The RF fields may be generated by transmitting/receiving coils of the MRI device and may be present during the MRI procedure. If the patient undergoing the MRI procedure has an implantable medical system, the various fields produced by the MRI device may have an effect on the operation of the medical leads and/or the IMD to which the leads are coupled. For example, the gradient magnetic fields or the RF fields generated during the MRI procedure may induce energy on the implantable leads.

SUMMARY

This disclosure provides a pacing technique that reduces the effect of EMI on pacing therapy. In the case of an MRI device, the gradient magnetic fields may induce energy on the lead that may, in some instances, coincide with delivery of a pacing pulse. In other words, the signal induced from the gradient magnetic field may be superimposed with the pacing signal delivered by the IMD. The induced energy on the pacing lead coinciding with the pacing pulse may either constructively interfere with the pacing pulse or destructively interfere with the pacing pulse. The interference is particularly problematic when the IMD provides unipolar pacing in the presence of the EMI. When the induced energy on the lead destructively interferes with the pacing pulse, there may be an increased risk that the energy from the pacing pulse falls below the capture threshold of the heart. In other words, the induced energy on the lead may increase the likelihood of the loss of capture.

An IMD operating in accordance with the pacing techniques of this disclosure may operate in an EMI operating mode in the presence of a noisy environment. While operating in the EMI operating mode, the IMD delivers a group of two or more pacing pulses in close proximity to one another instead of delivering conventional single pulse pacing. In one example, the IMD delivers a pair of pacing pulses with the second pacing pulse following immediately after the first pacing pulse of the pair and, at most, within 110 milliseconds of the first pacing pulse of the pair. If a gradient magnetic field of the MRI scan induces energy on the lead that destructively interferes with the first pacing pulse of the group (possibly resulting in loss of capture), one of the other pacing pulses of the group would pace the heart. In this manner, pacing the heart using groups of consecutive, closely spaced pacing pulses during exposure to EMI may decrease the risk for loss of capture. Moreover, the IMD does not have to increase the pacing pulse amplitude during exposure to the EMI, which may result in unintended muscle or nerve stimulation.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
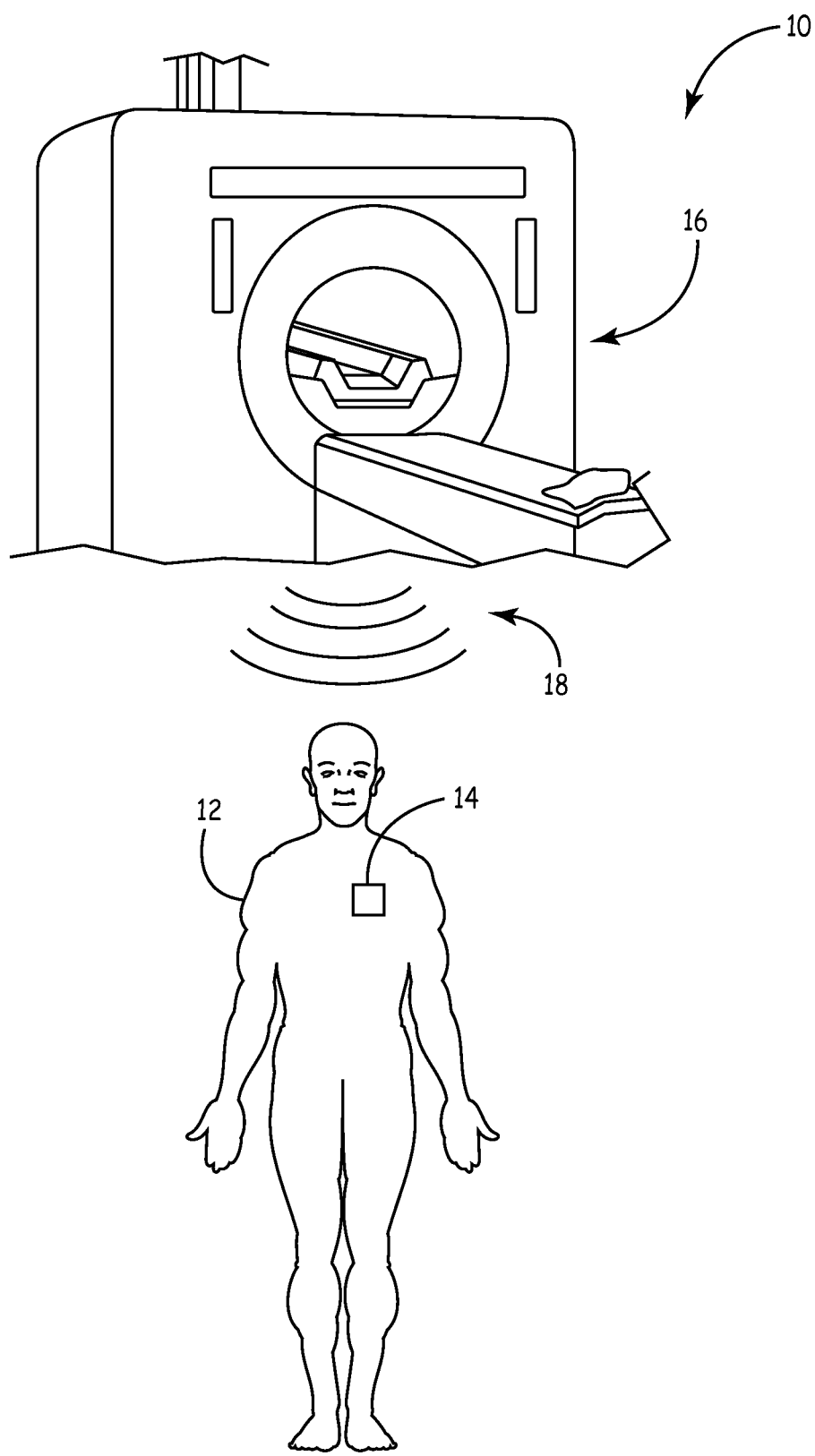
FIG. 1 is a conceptual diagram illustrating an environment in which a patient with an implantable medical system is exposed to external fields.

FIG. 1 is a conceptual diagram illustrating an environment 10 in which a patient 12 with an implantable medical system 14 is exposed to an external field 18. In the example illustrated in FIG. 1, environment 10 includes an MRI device 16 that generates external field 18. MRI device 16 generates magnetic and RF fields to produce images of body structures for diagnosing injuries, diseases and/or disorders. In particular, MRI device 16 generates a static magnetic field, gradient magnetic fields and RF fields as is well known in the art. The static magnetic field is a large non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field of about 1.5 Tesla (T) and have a corresponding RF frequency of about 64 megahertz (MHz) while a 3.0 T MRI device will produce a static magnetic field of about 3.0 Tesla and have a corresponding RF frequency of about 128 MHz. However, other MRI devices may generate different fields.

Implantable medical system 14 may, in one example, include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy.

During an MRI procedure patient 12 may be placed at least partially within a bore of MRI device 16. Some or all of the various types of fields produced by MRI device 16 (which are represented by external field 18) may create electromagnetic interference (EMI) that has undesirable effects on implantable medical system 14. In one example, the gradient magnetic fields and/or the RF fields generated during the MRI procedure may induce energy on the conductors of the leads (e.g., in the form of a current). The induced energy on the leads may interfere with delivery of pacing therapy.

In some instances, the energy induced on the lead by the gradient magnetic field may coincide with delivery of a pacing pulse. For example, the induced energy from the gradient magnetic field may be superimposed with the pacing energy delivered by the IMD. In this case, the induced energy on the pacing lead may either constructively interfere with the pacing pulse or destructively interfere with the pacing pulse. When the induced energy constructively interferes with the pacing pulse, the induced energy increases the energy associated with the pacing pulse. When the induced energy destructively interferes with the pacing pulse, however, the induced energy reduces the energy associated with the pacing pulse. When the induced energy on the lead destructively interferes with the pacing pulse, the reduced energy from the pacing pulse may, in some instances, fall below the capture threshold of the heart resulting in the loss of capture. The interference is particularly problematic when the IMD provides unipolar pacing in the presence of the EMI.

One potential solution to the destructive interference is to increase the amplitude of the unipolar pacing pulse. For example, the amplitude may be increased to a value that ensures capture even in the presence of the destructive interference. However, increasing the amplitude of the unipolar pacing pulse may increase the likelihood of unintended muscle or nerve stimulation, such as pectoral muscle stimulation adjacent to the location of IMD (sometimes referred to as pocket muscle stimulation) or diaphragmatic stimulation.

Implantable medical system 14 delivers unipolar pacing therapy in accordance with the pacing techniques of this disclosure to reduce the effect of EMI on delivery of pacing therapy. In particular, implantable medical system 14 reduces the likelihood of loss of capture due to the destructive interference of the gradient magnetic field induced energy while not increasing the likelihood of unintended muscle or nerve stimulation. As described in detail herein, implantable medical system 14 may deliver a group of two or more pacing pulses in close proximity to one another in place of conventional single pulse pacing while in the presence of EMI, e.g., while in environment 10. In one example, implantable medical system 14 delivers a pair of pacing pulses in close proximity to one another instead of the single pacing pulse conventionally delivered. The pair of pacing pulses may be within a few milliseconds of one another (e.g., within less than 5 milliseconds) and, at most, within 110 milliseconds of one another to avoid delivering one of the pacing pulses of the group during a vulnerable time (e.g., such as pacing on the T-wave).

Because the pacing therapy is provided as a group of two or more pacing pulses, the induced energy on the lead will not destructively interfere with all of the pacing pulses of the group. If gradient field induced energy destructively interferes with the first one of the pacing pulses of the group, one of the other pacing pulses would capture the heart. In this manner, pacing the heart using groups of pacing pulses during exposure to EMI instead of the single pacing pulse conventionally delivered may decrease the risk for loss of capture without increasing the likelihood of unintended muscle or nerve stimulation.

Figure 2:
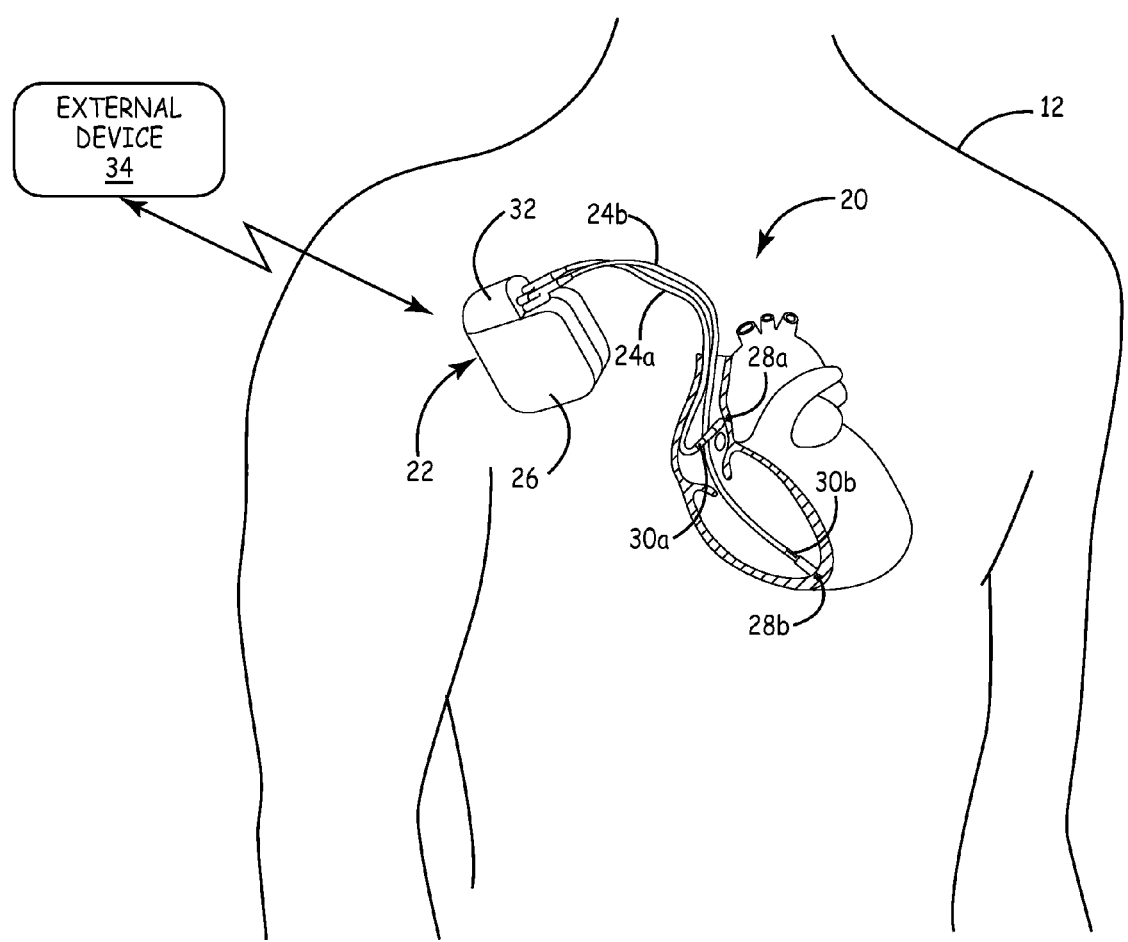
FIG. 2 is a conceptual diagram illustrating an example implantable medical system.

FIG. 2 is a conceptual diagram illustrating an example implantable medical system 20. Implantable medical system 20 may correspond with implantable medical system 14 of FIG. 1. Implantable medical system 20 includes an IMD 22 connected to leads 24a,b. IMD 22 includes a housing 26 within which electrical components and a power source of IMD 22 are housed. Housing 26 can be formed from conductive materials, non-conductive materials or a combination thereof. As will be described in further detail herein, housing 26 may house one or more processors, memories, transmitters, receivers, transceivers, sensors, sensing circuitry, therapy circuitry, antennas and other components.

Leads 24a,b each includes one or more electrodes. In the example illustrated in FIG. 2, leads 24a,b each include a respective tip electrode 28a,b and ring electrode 30a,b located near a distal end of their respective leads 24a,b. When implanted, tip electrodes 28a,b and/or ring electrodes 30a,b are placed relative to or in a selected tissue, muscle, nerve or other location within the patient 12. In the example illustrated in FIG. 2, tip electrodes 28a,b are extendable helically shaped electrodes to facilitate fixation of the distal end of leads 24a,b to the target location within patient 12. In this manner, tip electrodes 28a,b are formed to define a fixation mechanism. In other embodiments, one or both of tip electrodes 28a,b may be formed to define fixation mechanisms of other structures. In other instances, leads 24a,b may include a fixation mechanism separate from tip electrode 28a,b. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

Leads 24a,b are connected at a proximal end to IMD 22 via connector block 32. Connector block 32 may include one or more receptacles that interconnect with one or more connector terminals located on the proximal end of leads 24a,b. Leads 24a,b are ultimately electrically connected to one or more of the electrical components within housing 26. One or more conductors (not shown in FIG. 2) extend within leads 24a,b from connector block 32 along the length of the lead to engage the ring electrode 30a,b and tip electrode 28a,b, respectively. In this manner, each of tip electrodes 28a,b and ring electrodes 30a,b is electrically coupled to a respective conductor within its associated lead bodies. For example, a first electrical conductor can extend along the length of the body of lead 24a from connector block 32 and electrically couple to tip electrode 28a and a second electrical conductor can extend along the length of the body of lead 24a from connector block 32 and electrically couple to ring electrode 30a. The respective conductors may electrically couple to circuitry, such as a therapy module or a sensing module, of IMD 22 via connections in connector block 32.

IMD 22 delivers therapy to the heart (or other location) via the electrical conductors to one or more of electrodes 28a,b and 30a,b. In the case of pacing therapy, for example, IMD 22 may deliver pacing pulses via a unipolar electrode configuration, e.g., using electrodes 28a,b and a housing electrode of IMD 22. In other instances, IMD 22 may deliver pacing pulses via a bipolar electrode configuration, e.g., using electrodes 28a,b and ring electrodes 30a,b. IMD 22 may also receive sensed electrical signals on the electrical conductors from one or more of electrodes 28a,b and 30a,b. IMD 22 may sense the electrical signals using either a unipolar or bipolar electrode configuration.

IMD 22 may communicate with external device 34 to exchange data with external device 34. External device 34 may, for example, communicate with IMD 22 to provide one or more operating parameters for operation of IMD 22. In some instances, external device 34 may transmit a command to IMD 22 to configure IMD 22 into an EMI operating mode that provides pacing in accordance with the techniques described herein. IMD 22 may also transmit sensed physiological data, diagnostic determinations made based on the sensed physiological data, IMD performance data and/or IMD integrity data to external device 34. IMD 22 and external device 34 may communicate via wireless communication using any techniques known in the art. Examples of communication techniques may include, for example, inductive telemetry or RF telemetry, although other techniques are also contemplated.

The configuration of implantable medical system 20 illustrated in FIG. 2 is merely an example. In other examples, implantable medical system 20 may include more or fewer leads extending from IMD 22. For example, IMD 22 may be coupled to three leads, e.g., a third lead implanted within a left ventricle of the heart of the patient. In another example, IMD 22 may be coupled to a single lead that is implanted within either an atrium or ventricle of the heart of the patient. As such, IMD 22 may be used for single chamber or multi-chamber cardiac rhythm management therapy.

In addition to more or fewer leads, each of the leads may include more or fewer electrodes. In instances in which IMD 22 is used for therapy other than pacing, e.g., defibrillation or cardioversion, the leads may include elongated electrodes, which may, in some instances, take the form of a coil. IMD 22 may deliver defibrillation or cardioversion shocks to the heart via any combination of the elongated electrodes and housing electrode. As another example, medical system 20 may include leads with a plurality of ring electrodes, e.g., as used in some implantable neurostimulators, without a tip electrode or with one of the ring electrodes functioning as the "tip electrode."

Figure 3:
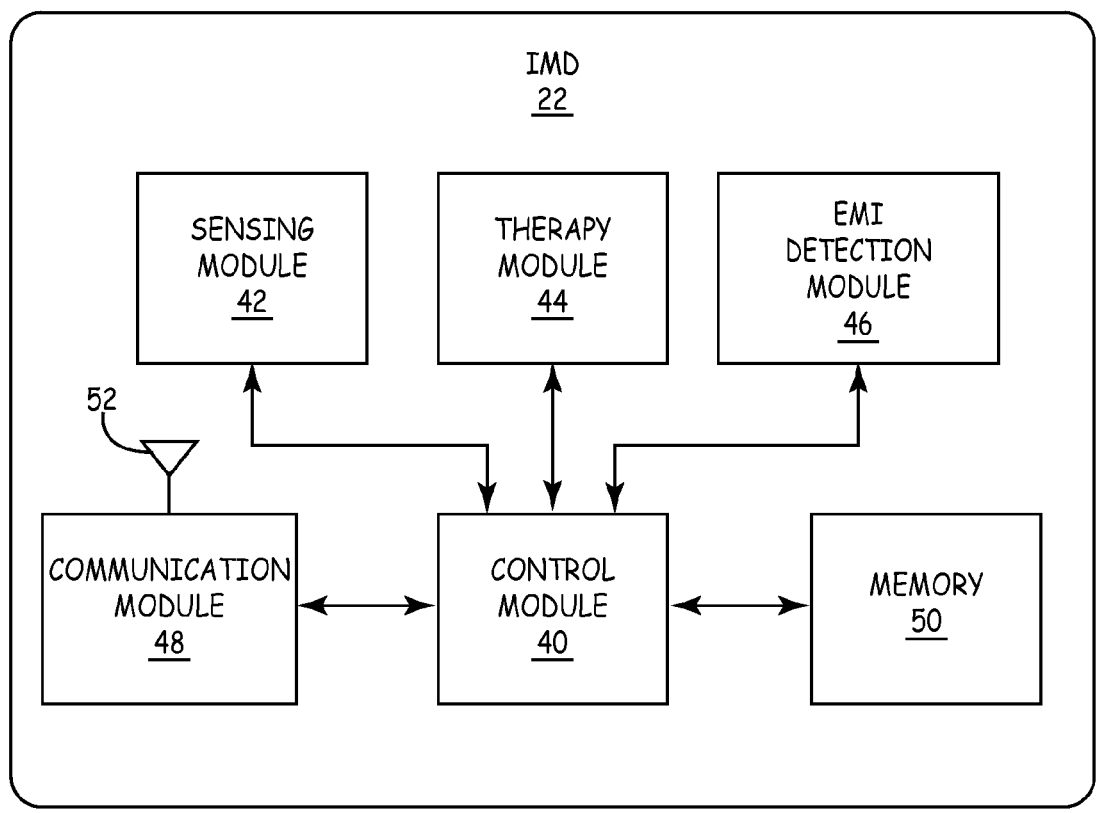
FIG. 3 is a functional block diagram of an example configuration of electronic components of an implantable medical device.

FIG. 3 is a functional block diagram of an example configuration of electronic components of IMD 22. IMD 22 includes a control module 40, sensing module 42, therapy module 44, magnetic field detection module 46, communication module 48, and memory 50. The electronic components may receive power from a power source (not shown in FIG. 3), which may be a rechargeable or non-rechargeable battery. In other embodiments, IMD 22 may include more or fewer electronic components. Additionally, any of the described modules or components may be implemented together on a common hardware component or separately as discrete but interoperable hardware or software components. Depiction of different features as modules or components is intended to highlight different functional aspects and does not necessarily imply that such modules or units must be realized by separate hardware or software components. Rather, functionality associated with one or more modules may be performed by separate hardware or software components, or integrated within common or separate hardware or software components.

Therapy module 44 is configured to generate and deliver electrical stimulation therapy to the heart. Therapy module 44 may include one or more pulse generators, capacitors, or other components capable of generating and/or storing energy to deliver as pacing pulses. Therapy module 44 is capable of delivering a group of two or more pacing pulses in close proximity to one another. In some instances, the two or more pacing pulses may be delivered immediately after one another. In other instances, the two or more pacing pulses may be delivered within a few milliseconds of one another. At most, the pacing pulses must be delivered within 110 milliseconds of one another to avoid pacing during a vulnerable time of the heart. In one example, the pacing pulses must be delivered within 5 milliseconds of one another. Control module 40 may control therapy module 44 to deliver electrical stimulation therapy to the heart via one or more of electrodes 28a,b and 30a,b according to one or more therapy programs, which may be stored in memory 50. Control module 40 controls therapy module 44 to deliver electrical pacing pulses, cardiac resynchronization pacing pulses, cardioversion pulses, or defibrillation pulses with the amplitudes, pulse widths, frequencies, electrode combinations or electrode configuration specified by a selected therapy program.

In the case of pacing therapy, for example, therapy module 44 may deliver pacing pulses via a bipolar electrode configuration, e.g., using electrodes 28a,b and ring electrodes 30a,b. In other instances, therapy module 44 may deliver pacing pulses via a unipolar electrode configuration, e.g., using electrodes 28a,b and a housing electrode of IMD 22. Therapy module 44 may include a switch module (not shown) that control module 40 may configure to select which of the available electrodes are used to deliver the stimulation therapy. Therapy module 44 may deliver one or more of these types of stimulation in the form of other signals besides pulses or shocks, such as sine waves, square waves, or other substantially continuous signals.

In some instances, the energy induced on lead 24 by gradient magnetic fields of MRI device 16 may coincide with delivery of one or more pacing pulses generated by therapy module 44. In this case, the induced energy on lead 24 may either constructively interfere with the pacing pulse or destructively interfere with the pacing pulse. When the induced energy on lead 24 destructively interferes with the pacing pulse, the reduced energy of the pacing pulse may fall below the capture threshold of the heart resulting in loss of capture. The interference is particularly problematic when the pacing therapy is delivered via a unipolar electrode configuration.

Control module 40 may detect a condition indicative IMD 22 being subjected to EMI having one or more particular characteristics. EMI detection module 46 of IMD 22 may include one or more sensors or be coupled to one or more sensors that monitor for the one or more particular characteristics of EMI. Control module 40 may use information provided by EMI detection module 46 alone or in conjunction with other information to determine whether IMD 22 is being subjected to EMI having the particular characteristic(s). EMI detection module 46 may include any type of sensor that provides information indicative of the characteristics of the EMI in the surrounding environment including, e.g., one or more Hall effect sensors, a reed switch, a magnetic gradient sensor, an antenna, a radiofrequency (RF) sensing device, or other sensors or combination of sensors.

As a specific example, control module 40 may use the information provided by EMI detection module 46 to determine whether IMD 22 is being subjected to external fields of MRI device 16. In this example, EMI detection module 46 monitors for EMI having particular characteristics associated with MRI device 16, e.g., particular magnetic field strengths, RF frequencies or gradient field characteristics. For instance, control module 40 may determine that IMD 22 is being subjected to external fields of MRI device 16 when an output of EMI detection module 46 indicates existence of a magnetic field having a strength greater than a threshold strength, e.g., greater than 1.0 Tesla. In other instances, control module 40 may make the determination based on other information from EMI detection module 46 in addition to or instead of the magnetic field strength.

In some embodiments, IMD 22 may not include an EMI detection module 46. Instead, IMD 22 may receive, via communication module 48, a communication from an external device (e.g., external device 34 of FIG. 2) indicating that IMD 22 is being exposed to or will soon be exposed to EMI, such as external fields 18 of MRI device 16. For example, control module 40 may receive a command to switch to the EMI operating mode. In this case, the communication or command from external device 34 may be considered the condition indicative of IMD 22 being subjected to EMI having one or more particular characteristics.

Communication module 48 includes any suitable hardware, firmware, software or any combination thereof for communicating with another device, such as external device 34, by wireless telemetry. For example, communication module 48 may include appropriate modulation, demodulation, frequency conversion, filtering, and amplifier components for transmission and reception of data with the aid of antenna 52. Antenna 52 may be located within connector block 32 of IMD 22 or within housing 26 of IMD 22. In one example, antenna 52 may be an inductive coil antenna within housing 26 of IMD 22. In another example, antenna 52 may be an RF antenna located within connector block 32 and coupled to communication module 48 via a feedthrough. In a further example, IMD 22 may include both an inductive coil antenna and an RF antenna coupled to communication module 48 or other antenna located within or outside of housing 26.

In response to detecting the condition indicative of IMD 22 being subjected to EMI having one or more particular characteristics, control module 40 transitions operation of IMD 22 from a current operating mode (e.g., a normal operating mode) to an EMI operating mode. In one example, the EMI operating mode may be an MRI-safe operating mode. In accordance with the pacing techniques of this disclosure, control module 40 may control therapy module 44 to generate and deliver a group of two or more unipolar pacing pulses in close proximity to one another in place of conventional single pulse pacing while operating in the EMI operating mode. Delivering the group of pacing pulses instead of the conventional single pacing pulse while in the presence of the EMI may reduce the effect of EMI on delivery of unipolar pacing therapy because the induced energy on lead 24 will not destructively interfere with all of the pacing pulses of the group.

In one example, control module 40 may control therapy module 44 to deliver a pair of pacing pulses in close proximity to one another instead of the single pacing pulse conventionally delivered. The second pacing pulse of the pair may occur almost immediately subsequent to the first pacing pulse. In some instances, the second pacing pulse of the pair of pacing pulses may be within a few milliseconds of the first pacing pulse. In one example, the second pacing pulse of the pair of pacing pulses may be within 5 milliseconds of the first pacing pulse. At most, however, the second pacing pulse should be within approximately 110 milliseconds of one another to avoid delivering the second pacing pulse of the pair during a vulnerable time (e.g., such as pacing on the T-wave). Although described in the context of a pair of pacing pulses, control module 40 may control therapy module 44 to deliver groups of more than two pacing pulses in close proximity to one another.

Since the gradient magnetic fields associated with the MRI scan are typically less than 1 millisecond in duration, the gradient field induced energy on the lead will not destructively interfere with all of the pacing pulses of the group. If gradient field induced energy destructively interferes with the first one of the pacing pulses of the group, one of the other pacing pulses (e.g., the second pacing pulse) would capture the heart. In this manner, pacing the heart using groups of pacing pulses during exposure to EMI instead of the single pacing pulse conventionally delivered may decrease the risk for loss of capture.

The amplitude of each of the pacing pulses of the group may be approximately the same as the amplitude of the conventional pacing pulse delivered in the normal mode of operation. In this case, all of the pacing pulses of the group may have substantially the same amplitude. As a result, the unipolar pacing techniques of this disclosure do not increase the chances of unintended muscle or nerve stimulation, such as pectoral and diaphragmatic stimulation, which may be associated with increased pacing amplitudes.

Control module 40 may suspend operation of other functionality of IMD 22 while operating in the EMI operating mode. For example, control module 40 may suspend tachycardia detection and therapy, fibrillation detection and therapy, impedance measurements, battery measurements, or the like. Control module 40 may perform some of the functions in a different manner. For example, control module 40 may use a different sensor or algorithm to detect cardiac activity of the heart of patient 12, such as pressure sensor measurements rather than electrical activity of the heart.

Sensing module 42 may include sensing components used to process signals received from electrodes 28*a,b* and 30*a,b*. The components of sensing module 42 may be analog components, digital components or a combination thereof. Sensing module 42 may include multiple sensing channels each having associated sensing components. Each sensing channel may, for example, include one or more sense amplifiers, filters, rectifiers, threshold detectors, analog-to-digital converters (ADCs) or the like. Some sensing channels may convert the sensed signals to digital form and provide the digital signals to control module 40 for processing or analysis. For example, sensing module 42 may amplify signals from the sensing electrodes and convert the amplified signals to multi-bit digital signals by an ADC. Other sensing channels may compare processed signals to a threshold to detect the existence of P- or R-waves and indicate the existence of the P- or R-waves to control module 40.

Sensing module 42 is electrically coupled to some or all of electrodes 28*a,b* and 30*a,b* via the conductors of leads 24*a,b*, or to a housing electrode (e.g., formed from or on housing 26) via conductors internal to housing 26. Sensing module 42 is configured to obtain signals sensed via one or more of electrodes 28*a,b* and 30*a,b* or the housing electrode. Control module 40 may select the electrodes that function as sense electrodes, sometimes referred to as a sensing configuration or sensing vector, in order to monitor electrical activity of the heart. In one example, sensing module 42 may include a switch module (not shown and which may be the same or different switch module described above with respect to therapy module 44) that control module 40 may configure to select which of the available electrodes to use for sensing the heart activity.

Control module 40 may process the signals from sensing module 42 to monitor electrical activity of the heart of patient 12. Control module 40 may store signals obtained by sensing module 42 as well as any generated EGM waveforms, marker channel data or other data derived based on the sensed signals in memory 50. Control module 40 may analyze the EGM waveforms and/or marker channel data to detect cardiac events (e.g., tachyarrhythmias). In further examples, sensing module 42 is coupled to one or more sensors that are not included on leads 24*a,b*, e.g., via a wired or wireless coupling. Such sensors may include pressure sensors, accelerometers, flow sensors, blood chemistry sensors, activity sensors, magnetic field sensors or other types of physiological sensors.

Control module 40 may, in some instances, control pacing therapy as a function of the sensed electrical signals when operating in the EMI operating mode. Control module 40 may utilize the sensed electrical signals obtained by sensing module 42 (or lack of sensed electrical signals) to trigger delivery of pacing pulses and/or inhibit delivery of pacing pulses. In other instances, control module 40 may control pacing therapy without regard to the sensed electrical signals on leads 24, sometimes referred to as asynchronous pacing, while operating in the EMI operating mode.

The various modules of IMD 22 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 50 may include computer-readable instructions that, when executed by control module 40 or other component of IMD 22, cause one or more components of IMD 22 to perform various functions attributed to those components in this disclosure. Memory 50 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

Figure 4:
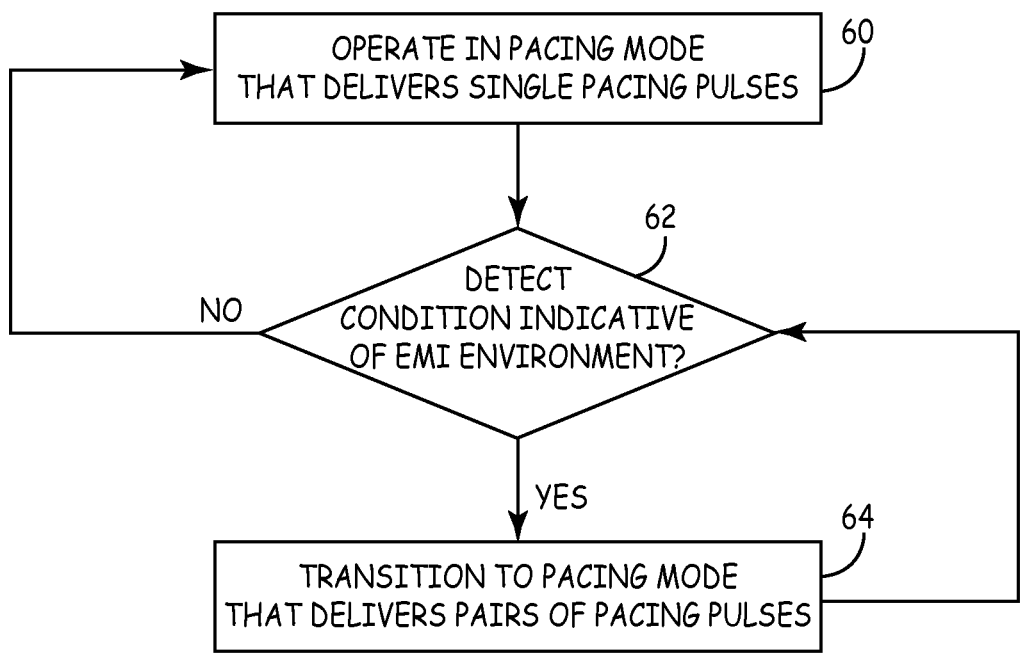
FIG. 4 is a flow diagram illustrating example operation of an implantable medical device operating in accordance with the techniques of this disclosure.

FIG. 4 is a flow diagram illustrating example operation of an implantable medical device operating in accordance with the techniques of this disclosure. Control module initially operates IMD 22 in accordance with a normal operating mode that delivers single pulse pacing (60). The normal operating mode may correspond with the operating mode that a physician or other user feels provides a most efficacious therapy for patient 12. The normal operating mode may vary from patient to patient depending on the condition of patient 12 for which IMD 22 is providing therapy. Control module 40 may control therapy module 44 to deliver any type of pacing therapy according to a variety of pacing techniques in the normal operating mode. For example, control module 40 may control therapy module 44 to deliver asynchronous pacing therapy, demand pacing therapy and/or rate-responsive pacing therapy. Control module 40 may deliver, for example, single-chamber pacing therapy, dual chamber pacing therapy, atrial pacing therapy, ventricular pacing therapy, bi-ventricular pacing therapy and/or multi-site pacing therapy. In some examples, control module 40 may control therapy module 44 to deliver pacing therapy in accordance with one or more of the pacing modes defined in the North American Society of Pacing and Electrophysiology (NASPE)/British Pacing and Electrophysiology Group (BPEG) Generic Pacemaker Code (NBG Code). The normal operating mode may also provide tachycardia detection and therapy, fibrillation detection and therapy, impedance measurements, battery measurements, or other function.

Control module 40 determines whether a condition indicative of IMD 22 being subjected to EMI having one or more particular characteristics is detected (62). In one instance, control module 40 may use information provided by EMI detection module 46 alone or in conjunction with other information to determine whether IMD 22 is being subjected to EMI having the particular characteristic(s). For example, control module 40 may determine that a condition indicative of IMD 22 being subjected to EMI exists when the output of EMI detection module 46 indicates existence of a magnetic field having a strength greater than a threshold strength, e.g., greater than 1.0 Tesla. Alternatively, control module 40 may determine a condition indicative of IMD 22 being subjected to EMI exists upon receiving a communication from external device 34 including a command to switch to the EMI operating mode.

When control module 40 does not detect the condition indicative of IMD 22 being subjected to EMI having one or more particular characteristics ("NO" branch of block 62), control module 40 continues to operate in the normal pacing mode. When control module 40 detects the condition indicative of IMD 22 being subjected to EMI having one or more particular characteristics ("YES" branch of block 62), control module 40 transitions operation of IMD 22 to an EMI operating mode that delivers groups of two or more pacing pulses instead of single pulse pacing (64). Delivering unipolar pacing therapy using groups of pacing pulses instead of single pacing pulses reduces the effect of EMI on delivery of pacing therapy. In particular, the gradient field induced energy on lead 24 will not destructively interfere with all of the pacing pulses of the group. As such, at least one of the pacing pulses of the group will capture the heart. In some instances, control module 40 may control therapy module 44 to generate and deliver the groups of pacing pulses each time a pacing pulse is delivered. In other instances, control module 40 may control therapy module 44 to generate and deliver the groups of pacing pulses only when a gradient magnetic field is determined to coincide with the timing at which the pacing pulse is delivered. In this case, control module 40 may control therapy module 44 to generate and deliver a single pacing pulse when no gradient magnetic field is determined to coincide with the time at which the pacing pulse is to be delivered since there is a small likelihood of interference when no gradient field is present.

As described above, control module 40 may suspend operation of or otherwise adjust other functionality of IMD 22 while operating in the EMI operating mode. For example, control module 40 may suspend tachycardia detection and therapy, fibrillation detection and therapy, impedance measurements, battery measurements, or the like. As another example, control module 40 may adjust functionality of IMD 22 by using a different sensor or algorithm to detect cardiac activity of the heart of patient 12.

Figure 5:
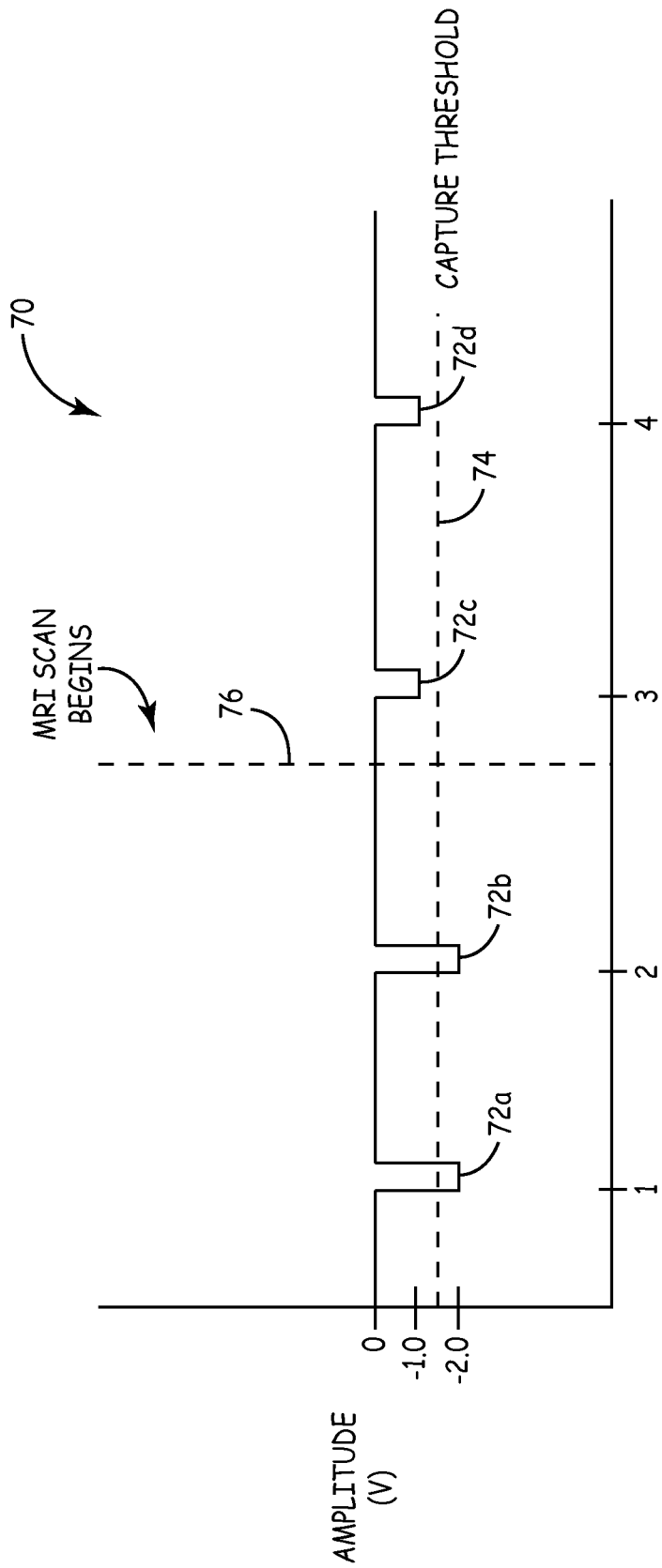
FIGS. 5-7 illustrate timing diagrams of pacing in the presence of EMI.
Figure 6:
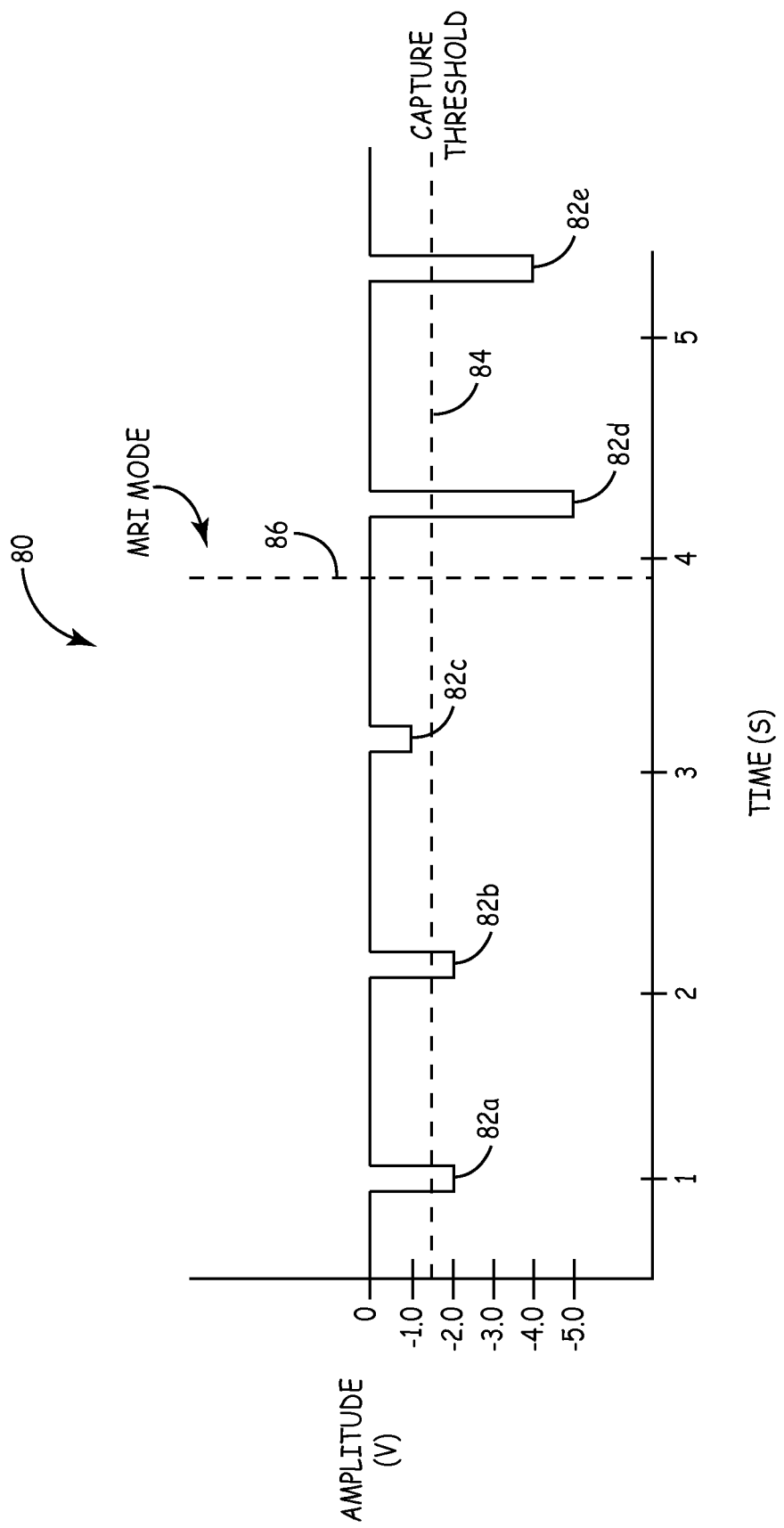
Figure 7:
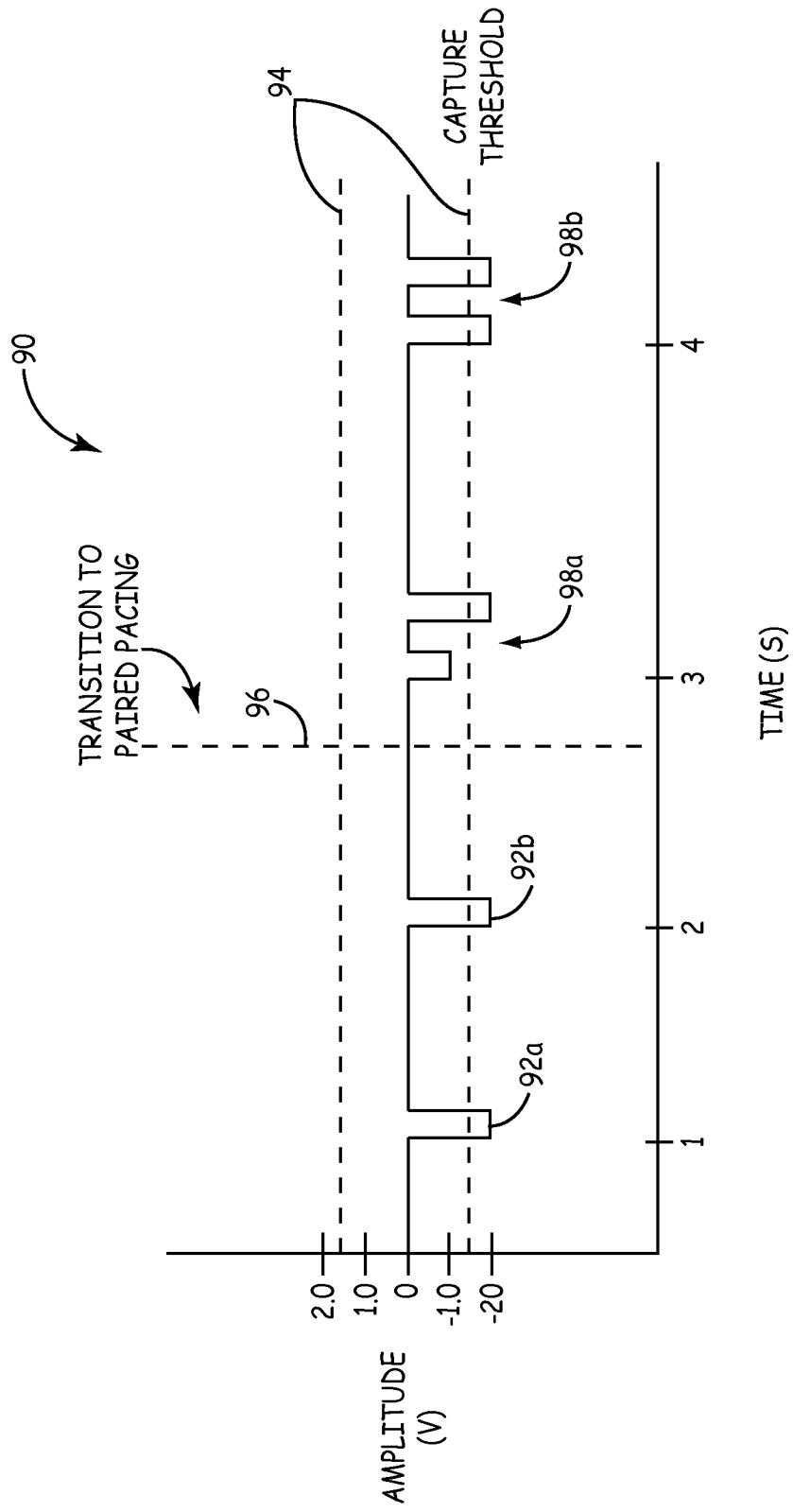

FIGS. 5-7 illustrate timing diagrams of pacing in the presence of EMI. The amplitudes, pulse widths, capture thresholds and other parameters are illustrated for purposes of illustration. The techniques of this disclosure are not limited to such amplitudes, pulse widths, or capture thresholds. These values are provided solely for purposes of illustration of the techniques.

FIG. 5 is a timing diagram 70 illustrating pacing energy on a lead 24. In the example illustrated in FIG. 5, IMD 22 provides asynchronous unipolar pacing therapy at a pacing rate of sixty beats per minute. However, the techniques of this disclosure are not limited to asynchronous pacing. The pacing techniques of this disclosure may be used in the context of synchronous pacing that triggers and/or inhibits delivery of pacing as a function of sensed cardiac electrical signals.

To achieve an asynchronous pacing rate of sixty beats per minute, IMD 22 delivers one of pacing pulses 72a-d every second. In the example illustrated in FIG. 5, IMD 22 is configured to deliver single pacing pulses having a negative phase, an amplitude of −2.0 volts (V) and a pulse width of approximately 1 millisecond. The amplitude of the pacing pulses provided by IMD 22 is above a measured capture threshold of the heart, which corresponds with dotted line 74 (labeled "CAPTURE THRESHOLD") and is equal to approximately −1.5V. Again, the values are provided solely for purposes of illustration of the techniques and should not be considered limiting of the techniques described herein.

In the example of FIG. 5, dotted line 76 represents the time at which an MRI scan begins. Prior to the start of the MRI scan, pacing pulses 72a and 72b are delivered at the desired pulse amplitude, e.g., −2.0V in the illustrated example. However, one or more of the pacing pulses subsequent to the start of the MRI scan may not be delivered at the desired pulse amplitude due to interference from a current induced on leads 24 by gradient magnetic fields of MRI device 16. As described above, the gradient magnetic fields may induce a current on leads 24, which in some instances, may coincide with delivery of one or more pacing pulses. In this case, the induced energy from the MRI fields may either constructively interfere with one or more of the pacing pulses or destructively interfere with one or more of the pacing pulses. In the example illustrated in FIG. 5, the induced energy on lead 24 destructively interferes with pacing pulses 72c and 72d, resulting in pacing pulses having a reduced amplitude. In the example illustrated in FIG. 5, the reduced amplitude of pacing pulses 72c and 72d is approximately −1.0V, which is less than the capture threshold of the heart. As a result, the interference of the MRI fields may result in loss of capture for at least pacing pulses 72c and 72d.

FIG. 6 is a timing diagram 80 illustrating one technique for reducing the interference of the MRI fields on unipolar pacing therapy. In the example illustrated in FIG. 6, IMD 22 again provides asynchronous pacing pulses 82a-e ("pacing pulses 82") at a pacing rate of sixty beats per minute. As with pacing pulses 72 illustrated in FIG. 5, pacing pulses 82 are single pacing pulses. However, IMD 22 generates pacing pulses having different amplitudes depending on whether IMD 22 is operating in a normal operating mode or an EMI operating mode. In the example of FIG. 6, dotted line 86 represents the time at which IMD 22 begins operating in the EMI operating mode. In other words, IMD 22 operates in the normal operating mode prior to the time corresponding to dotted line 86 and operates in the EMI operating mode after the time corresponding to dotted line 86.

While operating in the normal operating mode, IMD 22 generates pacing pulses 82a-c having negative phases, amplitudes of −2.0V and pulse widths of approximately 1 millisecond. The amplitude of pacing pulses 82a-c are above the capture threshold of the heart, which corresponds with dotted line 84 (labeled "CAPTURE THRESHOLD") and is equal to approximately −1.5V in the illustrated example. Upon switching to the EMI operating mode, however, IMD 22 generates pacing pulses 82d and 82e having increased amplitudes. In the example illustrated in FIG. 6, IMD 22 generates pacing pulses 82d and 82e with amplitudes of approximately −5.0V.

Generating and delivering pacing pulses having increased amplitudes reduces the likelihood of energy induced on leads 24 by the gradient magnetic fields reducing the amplitude of the pacing pulses to a value below the capture threshold. For example, the induced energy on lead 24 destructively interferes with pacing pulse 82e. In the example illustrated in FIG. 6, the destructive interference reduces the amplitude of pacing pulse 82e from approximately −5.0V to approximately −4.0V. However, pacing pulse 82e has an initial amplitude that is large enough so, even with the destructive interference caused by the MRI fields, pacing pulse 82e remains above the capture threshold so there is no loss of capture. Pacing pulse 82d does not experience any interference (constructive or destructive) with induced energy in the example illustrated in FIG. 6.

Although such a technique decreases the likelihood of loss of capture during pacing therapy, the pacing therapy may consume more power than the normal pacing mode. Additionally, the increased amplitude of the pacing pulses may increase the chances of unintended muscle or nerve stimulation, such as pectoral and diaphragmatic stimulation, particularly when energy induced on lead 24 by the MRI fields constructively interferes with the pacing pulses.

FIG. 7 is a timing diagram 90 illustrating another technique for reducing the interference of the MRI fields on pacing therapy. In the example illustrated in FIG. 7, IMD 22 again provides unipolar pacing pulses 92a,b ("pacing pulses 92") and 98a,b ("pacing pulses 98") at a pacing rate of sixty beats per minute. As described in this disclosure, IMD 22 generates unipolar pacing therapy differently depending on whether IMD 22 is operating in a normal operating mode or an EMI operating mode. In the example of FIG. 7, dotted line 96 represents the time at which IMD 22 begins operating in the EMI operating mode. In other words, IMD 22 operates in the normal operating mode prior to the time corresponding to dotted line 96 and operates in the EMI operating mode after the time corresponding to dotted line 96.

While operating in the normal operating mode, IMD 22 generates single pacing pulses 92a and 92b having negative phases, amplitudes of −2.0V and pulse widths of approximately 1 millisecond. The amplitude of pacing pulses 92a and 92b are above the capture threshold of the heart, which corresponds with dotted lines 94 (labeled "CAPTURE THRESHOLD") and is equal to approximately ±1.5V in the illustrated example.

Upon switching to the EMI operating mode, however, IMD 22 generates groups of two pacing pulses in close proximity to one another. FIG. 7 illustrates a first group 98a of pacing pulses that includes two pacing pulses in close proximity to one another and a second group 98b of pacing pulses that includes two pacing pulses in close proximity to one another. Although described in the context of a pair of pacing pulses, control module 40 may control therapy module 44 to deliver groups of more than two pacing pulses in close proximity to one another.

Since the gradient magnetic fields associated with the MRI scan are typically less than 1 millisecond in duration, the gradient field induced energy on the lead will not destructively interfere with all of the pacing pulses of groups 98 of pacing pulses. If gradient field induced energy destructively interferes with the first one of the pacing pulses of group 98a, the second pacing pulse of the group 98a would capture the heart. In this manner, pacing the heart using groups of pacing pulses during exposure to EMI instead of the single pacing pulse conventionally delivered may decrease the risk for loss of capture.

Moreover, by utilizing groups of pacing pulses, IMD 22 does not need to significantly increase the amplitude of the pacing pulses while functioning in the EMI operating mode. Instead, IMD 22 may generate the pacing pulses of the groups with approximately the same amplitude as the pacing pulses used during the normal operating mode. Thus, the pacing pulses delivered during the EMI operating mode do not increase the chances of unintended muscle or nerve stimulation, such as pectoral and diaphragmatic stimulation.

Figure 8:
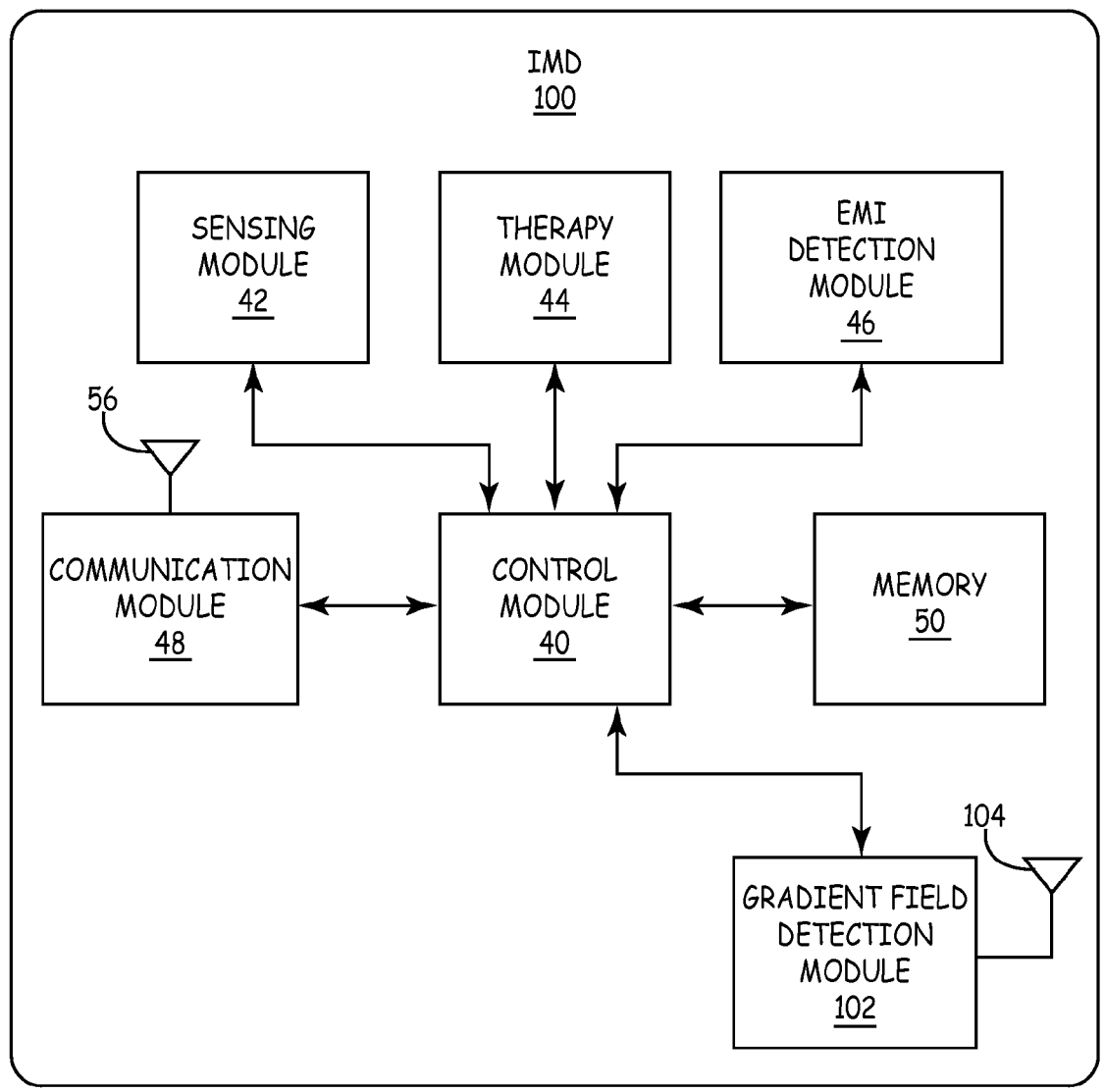
FIG. 8 is a block diagram illustrating another example configuration of electronic components of another implantable medical device.

FIG. 8 is a block diagram illustrating another example configuration of electronic components of an IMD 100. IMD 100 may correspond with IMD 22 of FIG. 2. IMD 100 conforms substantially to IMD 22 illustrated in FIG. 3, but includes a gradient field detection module 102.

Gradient field detection module 102 of IMD 100 detects gradient magnetic fields separately from the noise-induced signals detected on leads 24a,b. Gradient field detection module 102 may, for example, receive noise signals by means of at least one antenna 104 capable of detecting gradient magnetic fields. Antenna 104 of gradient field detection module 102 may be the same as antenna 56 of communication module 48, e.g., an inductive coil antenna. For example, the signal received on antenna 56/104 may be divided and provided to communication module 48 and gradient field detection module 102. In another example, gradient field detection module 102 and communication module 48 may be a single module that analyzes the signals received on the antenna. Thus, noise signals that are induced in the telemetry antenna are detected and appropriately processed as described in further detail herein.

In another example, antenna 104 may be at least one separate, dedicated antenna. One example antenna is described in U.S. Pat. No. 7,693,568 to Zeijlemaker, which is incorporated herein for its description of transducer 40 that detects MRI gradient magnetic fields. Transducer 40 of the '568 patent can detect an MRI gradient magnetic field via inductive coupling of the field with one of three orthogonal coils 41, 42, 43 depending upon the orientation of the field. Coils 41, 42, 43 of transducer 40 of the '568 patent are sensitive enough to detect small changes in the magnetic field, for example, between approximately 5 Tesla per second and approximately 300 Tesla per second.

In other instances, antenna 104 may be a different one of leads 24. For example, an atrial lead may be utilized as gradient field antenna for adjusting ventricular pacing on a ventricular lead. In another example, antenna 104 may be a different sensing vector on the same lead on which the pacing therapy is being provided. In either of these cases, gradient field detection module 102 may be a part of the sensing module 42.

Control module 40 may control the pacing pulses delivered based on the output of gradient field detection module 102. While operating in the EMI operating mode, for example, control module 40 may control therapy module 44 to deliver single pacing pulses when no gradient magnetic field is detected to coincide with the timing of the pacing pulse and deliver groups of two or more pacing pulses when a gradient magnetic field is detected and coincides with the timing of the pacing pulse. Thus, control module 40 may monitor the output of gradient field detection module 102 just prior to generating and delivering pacing therapy to determine whether to generate a single pacing pulse or a group of pacing pulses. In this manner, groups of pacing pulses are only delivered when EMI exists that may interfere with a single pacing pulse, thus conserving energy. In some instances, control module 40 may control the pacing pulses delivered based on noise detected via gradient field detection module 102 in the normal operating mode.

Figure 9:
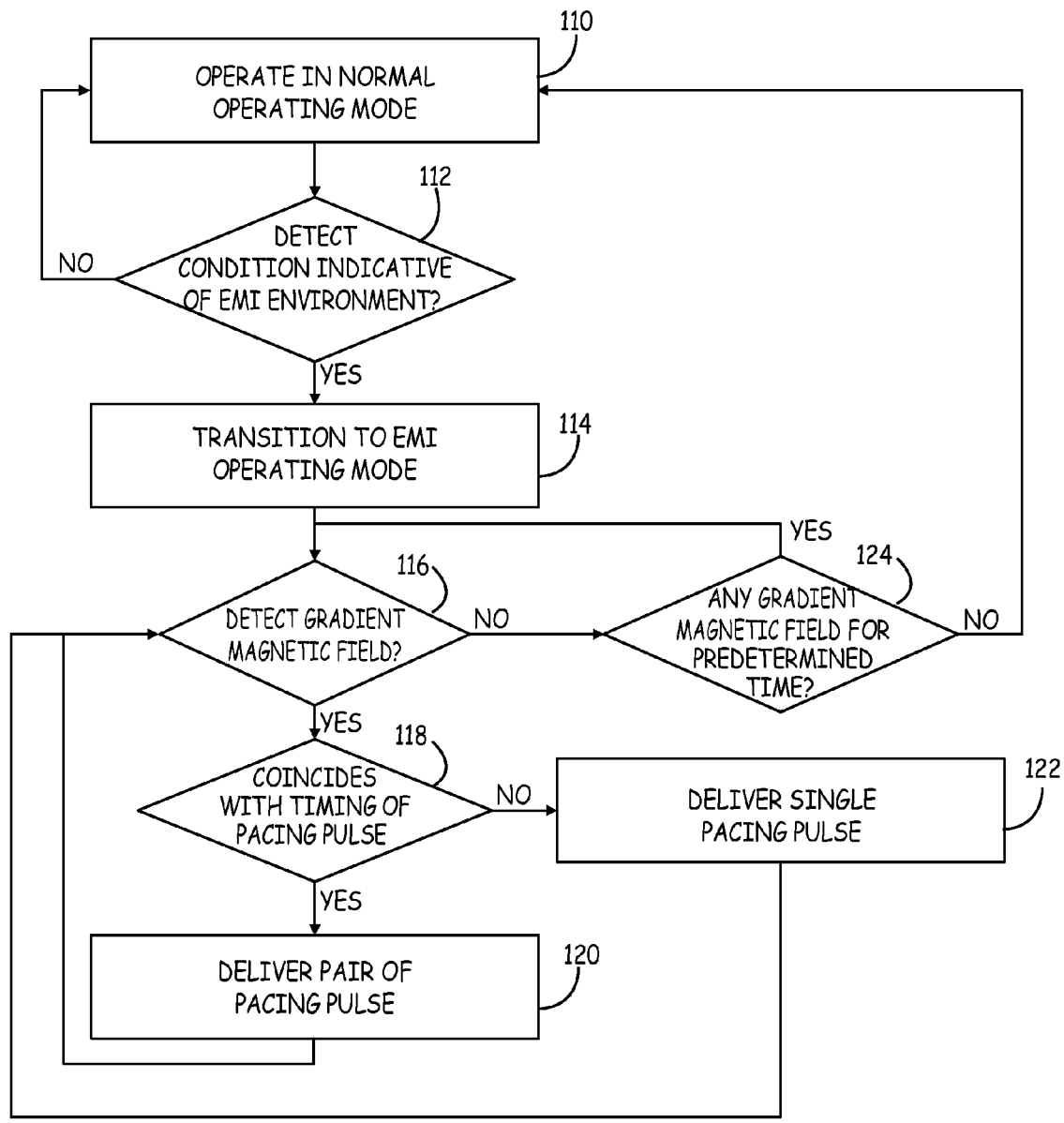
FIG. 9 is a flow diagram illustrating example operation of an IMD controlling the delivery of paired pacing pulses based on the detection of gradient magnetic fields coinciding with the timing of the pacing pulse.

FIG. 9 is a flow diagram illustrating example operation of an IMD, such as IMD 100, controlling the delivery of unipolar pacing therapy based on the detection of gradient magnetic fields coinciding with the timing of the pacing pulse. Control module 40 initially operates IMD 100 in accordance with a normal operating mode that delivers single pacing pulses (110). As described above, the normal operating mode may correspond with the operating mode that a physician or other user feels provides a most efficacious therapy for patient 12.

Control module 40 determines whether a condition indicative of IMD 22 being subjected to EMI having one or more particular characteristics is detected (112). In one instance, control module 40 may use information provided by EMI detection module 46 alone or in conjunction with other information to determine whether IMD 100 is being subjected to EMI having the particular characteristic(s). Alternatively, control module 40 may determine a condition indicative of IMD 100 being subjected to EMI exists upon receiving a communication from external device 34 including a command to switch to the EMI operating mode.

When control module 40 does not detect the condition indicative of IMD 100 being subjected to EMI having one or more particular characteristics ("NO" branch of block 112), control module 40 continues to operate in the normal pacing mode. When control module 40 detects the condition indicative of IMD 100 being subjected to EMI having one or more particular characteristics ("YES" branch of block 112), control module 40 transitions operation of IMD 100 to an EMI operating mode (114). The EMI operating mode may reduce the effect of EMI on delivery of pacing therapy. Control module 40 determines whether a gradient magnetic field is detected (116).

Control module 40 may determine whether a gradient magnetic field is present based on the output of gradient field detection module 100. When control module 40 detects the presence of a gradient magnetic field ("YES" branch of block 116), control module 40 determines whether the detected gradient magnetic field coincides with the timing of a pacing pulse (118). In one instance, control module 40 may monitor the output of gradient field detector 102 just prior to generating and delivering a pacing pulse and determine that the gradient magnetic field coincides with the timing of the pacing pulse if a gradient field is detected. In another example, control module 40 may compare the time at which the gradient magnetic field is sensed with the time at which the pacing pulse is to be delivered to determine whether the gradient magnetic field coincides with the time of the pacing pulse. The two signals may be coincident as long as they occur within a threshold period of time of one another, e.g., within 10 ms of one another. However, values larger or smaller than 10 ms may be used.

When control module 40 determines that the detected gradient magnetic field coincides with the timing of a pacing pulse ("YES" branch of block 118), control module 40 controls therapy module 44 to deliver a group of two or more pacing pulse (120). When control module 40 determines that the detected gradient magnetic field does not coincide with the timing of a pacing pulse ("NO" branch of block 118), control module 40 controls therapy module 44 to deliver a single pacing pulse (122). In this manner, IMD 100 only delivers groups of pacing pulses in place of a single pacing pulse when the gradient magnetic fields of the MRI device or other source has an increased likelihood of interfering with delivery of a single pacing pulse.

When control module 40 does not detect the presence of a gradient magnetic field ("NO" branch of block 116), control module 40 determines whether any gradient magnetic field has been detected during a predetermined period of time (124). In other instances, control module 40 may determine whether any condition indicative of the EMI environment has been detected during the predetermined period of time. Other conditions indicative of the EMI environment include a large magnetic field, RF signals at particular frequencies or the like. Additionally, the predetermined period of time may be selected to be a duration during which at least one noise signal would likely be received in a noisy environment. In one example, the predetermined period of time may be around ten minutes. However, the predetermined period of time may be greater than or less than ten minutes. When any gradient magnetic field has been detected during the predetermined period of time ("YES" branch of block 124), IMD 100 continues to monitor for gradient magnetic fields at block 116. When no gradient magnetic field has been detected during the predetermined period of time ("NO" branch of block 124), control module 40 operates IMD 100 in the normal operating mode (110).

The techniques described herein may be applicable to other therapy systems. For example, the techniques described herein may be applicable to systems including an IMD that delivers electrical stimulation therapy to other muscles, nerves or organs of patient 12. As another example, the techniques described herein may be applicable to systems including an implantable drug delivery or infusion device or an IMD including a drug delivery or infusion module. Other combinations of implantable devices will be obvious to one of skill in the art, and fall within the scope of this disclosure.

The techniques described in this disclosure, including those attributed to IMD 22, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, or flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   generating single stimulation pulses while operating an implantable medical device (IMD) in a first operating mode;
   detecting a condition indicative of the presence of electromagnetic interference (EMI);
   switching the IMD from the first operating mode to a second operating mode in response to detecting the condition indicative of the presence of EMI, wherein the second operating mode comprises an asynchronous pacing mode in which pacing therapy is delivered without regard to sensed electrical signals; and
   generating at least one group of two or more stimulation pulses in close proximity to one another while operating the IMD in the second operating mode, wherein the two or more stimulation pulses of the group are within 110 milliseconds of one another.

2. The method of claim 1, wherein the two or more stimulation pulses of the group are within 5 milliseconds of one another.

3. The method of claim 1, wherein generating the group of two or more stimulation pulses comprises generating two or more stimulation pulses having amplitudes that are substantially the same as one another.

4. The method of claim 1, wherein detecting the condition indicative of the presence of EMI comprises detecting the condition indicative of the presence of EMI based on information provided by one or more sensors.

5. The method of claim 4, wherein detecting the condition indicative of the presence of EMI based on information provided by one or more sensors comprises detecting the condition indicative of the presence of EMI when the output provided by the one or more sensors indicates that the strength of a magnetic field exceeds a threshold strength.

6. The method of claim 1, wherein detecting the condition indicative of the presence of EMI comprises receiving a command via wireless telemetry that instructs the IMD to switch into the second operating mode.

7. The method of claim 1, further comprising suspending at least one of tachycardia detection, tachycardia therapy, fibrillation detection, fibrillation therapy, impedance measurements, or battery measurements while operating in the second operating mode.

8. The method of claim 1, further comprising:
   detecting gradient magnetic fields while operating in the second operating mode; and
   delivering unipolar pacing therapy as a function of the detected gradient magnetic fields.

9. The method of claim 8, further comprising:
   determining whether a detected gradient magnetic field coincides with a timing of a stimulation pulse;
   delivering a single stimulation pulse when the detected gradient magnetic field does not coincide with the timing of the stimulation pulse; and
   delivering a group of two or more stimulation pulses when the detected gradient magnetic field does coincide with the timing of the stimulation pulse.

10. The method of claim 9, wherein determining whether the detected gradient magnetic field coincides with the timing of the desired stimulation pulse comprises:
    monitoring the output of a gradient field detection module just prior to the desired stimulation pulse; and
    determining that the gradient magnetic field coincides with the timing of the desired stimulation pulse if the gradient field is detected during the monitoring.

11. The method of claim 9, wherein determining whether the detected gradient magnetic field coincides with the timing of the desired stimulation pulse comprises determining that the gradient magnetic field coincides with the timing of the desired stimulation pulse if the gradient magnetic field and the desired stimulation pulse occur within a threshold period of time of one another.

12. The method of claim 11, wherein the threshold period of time is ten milliseconds.

13. An implantable medical system comprising:
    an implantable medical lead including at least one electrode;
    an implantable medical device comprising:
       an electromagnetic interference (EMI) detection module that monitors for one or more particular characteristics of EMI;
       a therapy module that delivers pacing therapy via the implantable medical lead;
       a control module that controls the therapy module to generate single stimulation pulses while operating the IMD in a first operating mode, detects a condition indicative of EMI based on the one or more monitored characteristics, switches the IMD from the first operating mode to a second operating mode in response to detecting the condition indicative of the presence of EMI, and controls the therapy module to generate at least one group of two or more stimulation pulses within 110 milliseconds of one another while operating the IMD in the second operating mode; and
       a gradient field detection module that detects gradient magnetic fields while operating in the second operating mode,
       wherein the control module determines whether a detected gradient magnetic field coincides with a timing of a desired stimulation pulse, controls therapy module to generate a single stimulation pulse when the detected gradient magnetic field does not coincide with the timing of the desired stimulation pulse, and controls therapy module to generate the at least one group of two or more stimulation pulses when the detected gradient magnetic field does coincide with the timing of the desired stimulation pulse.

14. The system of claim 13, wherein the control module generates the two or more stimulation pulses of the group within 5 milliseconds of one another.

15. The system of claim 13, wherein the control module controls the therapy module to generate the two or more stimulation pulses of the group with amplitudes that are substantially the same as one another.

16. The system of claim 13, further comprising one or more sensors that generate an output as a function of the EMI, wherein the control module detects the condition indicative of the presence of EMI based on the output of the one or more sensors.

17. The system of claim 13, further comprising a communication module that receives communications from an external device, wherein the control module detects the condition indicative of the presence of EMI by receiving a command via wireless telemetry that instructs the IMD to switch into the second operating mode.

18. The system of claim 13, wherein the control module suspends at least one of tachycardia detection, tachycardia therapy, fibrillation detection, fibrillation therapy, impedance measurements, or battery measurements while operating in the second operating mode.

19. The system of claim 13, wherein the control module monitors the output of the gradient field detection module just prior to the desired stimulation pulse and determines that the gradient magnetic field coincides with the timing of the desired stimulation pulse if the gradient field is detected.

20. The system of claim 13, wherein the control module determines that the gradient magnetic field coincides with the timing of the desired stimulation pulse if the gradient magnetic field and the desired stimulation pulse occur within a threshold period of time of one another.

21. The system of claim 20, wherein the threshold period of time is ten milliseconds.

22. A computer-readable medium comprising instructions that, when executed, cause an implantable medical device (IMD) to:
    generate single stimulation pulses while operating the IMD in a first operating mode;
    detect a condition indicative of the presence of electromagnetic interference (EMI);
    switch the IMD from the first operating mode to a second operating mode in response to detecting the condition indicative of the presence of EMI; and
    generate a group of two or more stimulation pulses within 110 milliseconds of one another each time a pacing pulse is desired while operating the IMD in the second operating mode.

23. The computer-readable medium of claim 22, wherein the instructions to generate the group of two or more stimulation pulses comprises instructions to generate within 5 milliseconds of one another.

24. The computer-readable medium of claim 22, wherein the instructions to generate the group of two or more stimulation pulses while operating in the second operating mode comprise instructions to generate the two or more stimulation pulses of the group with substantially the same amplitude as one another.

25. The computer-readable medium of claim 22, wherein the instructions to detect the condition indicative of the presence of EMI comprise instructions to detect the condition indicative of the presence of EMI based on one of information provided by one or more sensors and a command via wireless telemetry that instructs the IMD to switch into the second operating mode.

26. The computer-readable medium of claim 22, further comprising instructions that, when executed, cause the IMD to suspend at least one of tachycardia detection, tachycardia therapy, fibrillation detection, fibrillation therapy, impedance measurements, or battery measurements while operating in the second operating mode.

* * * * *